United States Patent
Schmieding et al.

(10) Patent No.: US 10,213,461 B2
(45) Date of Patent: Feb. 26, 2019

(54) COMBINED AUTOLOGOUS BIOLOGIC AND COLD THERAPY TREATMENT OF SKIN INJURIES

(71) Applicant: ARTHREX, INC., Naples, FL (US)

(72) Inventors: Reinhold Schmieding, Naples, FL (US); James P. Bradley, Pittsburgh, PA (US); Patrick A. Smith, Columbia, MO (US)

(73) Assignee: Arthrex, Inc, Naples, FL (US)

( * ) Notice: Subject to any disclaimer, the term of this patent is extended or adjusted under 35 U.S.C. 154(b) by 626 days.

(21) Appl. No.: 14/833,659

(22) Filed: Aug. 24, 2015

(65) Prior Publication Data

US 2017/0056446 A1    Mar. 2, 2017

(51) Int. Cl.
    *A61K 35/14*      (2015.01)
    *A01N 1/02*       (2006.01)
    *A61F 7/00*       (2006.01)
    *A61M 1/02*       (2006.01)

(52) U.S. Cl.
    CPC ............ *A61K 35/14* (2013.01); *A01N 1/0263* (2013.01); *A61F 7/0085* (2013.01); *A61M 1/0277* (2014.02); *A61M 2007/0052* (2013.01); *A61M 2202/0427* (2013.01); *A61M 2205/6009* (2013.01)

(58) Field of Classification Search
    CPC .............. B01L 3/5085; B01L 3/50851; B01L 3/50853; A23G 9/08; A23G 9/26; A61K 35/14
    See application file for complete search history.

(56) References Cited

U.S. PATENT DOCUMENTS

| 2,175,324 | A | * | 10/1939 | Stamp | ...................... A23G 9/26 249/120 |
| 2,702,011 | A | * | 2/1955 | Larkin | ...................... A23G 9/26 249/120 |
| 3,844,525 | A | | 10/1974 | Parmett | |
| 4,899,976 | A | | 2/1990 | Cederroth et al. | |

(Continued)

FOREIGN PATENT DOCUMENTS

EP    0341467        11/1989
EP    2574350 A1     4/2013

(Continued)

OTHER PUBLICATIONS

Extended European Search Report for European Application No. 16 18 5385.8 dated Jan. 2, 2017.

(Continued)

*Primary Examiner* — Jill A Warden
*Assistant Examiner* — Dwayne K Handy
(74) *Attorney, Agent, or Firm* — Carlson, Gaskey & Olds, P.C.

(57) ABSTRACT

This disclosure describes a combined autologous biologic and cold therapy treatment for treating various skin injuries. The treatment may include applying autologous blood components, including but not limited to platelet rich plasma, to a skin injury in a manner that influences the healing process. A tray assembly for freezing autologous blood components includes a tray body and a plurality of compartments formed in the tray body. Each of the plurality of compartments is configured to receive an individual dose of an autologous blood component.

2 Claims, 7 Drawing Sheets

(56) References Cited

U.S. PATENT DOCUMENTS

| | | | |
|---|---|---|---|
| 7,811,558 B2 | 10/2010 | Ho et al. | |
| 8,052,969 B2 | 11/2011 | Buhr et al. | |
| 8,618,258 B2 | 12/2013 | Yayon et al. | |
| 8,637,066 B2 | 1/2014 | Binnette et al. | |
| 8,821,858 B2 | 9/2014 | Gandy et al. | |
| 2003/0088657 A1* | 5/2003 | Eggers | G06F 19/366 709/223 |
| 2006/0039991 A1 | 2/2006 | Barrueta et al. | |
| 2009/0050784 A1* | 2/2009 | Slappay | F25C 1/24 249/203 |
| 2009/0060975 A1 | 3/2009 | Teets et al. | |
| 2010/0178314 A1* | 7/2010 | Yayon | A61K 9/0024 424/426 |
| 2011/0318404 A1 | 12/2011 | Kushnir et al. | |
| 2012/0156184 A1 | 6/2012 | Prochazka et al. | |
| 2013/0011530 A1* | 1/2013 | Wolf | A23G 9/26 426/241 |
| 2014/0121640 A1 | 5/2014 | Evans et al. | |
| 2014/0277452 A1 | 9/2014 | Skaer | |

FOREIGN PATENT DOCUMENTS

| | | |
|---|---|---|
| EP | 1848447 B1 | 11/2014 |
| WO | 2010086848 | 8/2010 |

OTHER PUBLICATIONS

Alice Roffi, et al: "Does Platelet-Rich Plasma Freeze-Thawing Influence Growth Factor Release and Their Effects on Chondrocytes and Synoviocytes?", Biomed Research International, vol. 5, No. 96, Jul. 17, 2014 (Jul. 17, 2014), pp. 423-510, XP055329455, US ISSN: 2314-6133, DOI: 10.1007/s00167-011-1837-x * 2. Materials and Methods 3. Results *.

Lacerum® Frozen Equine PRP Gel; Copyright 2014—PRP Technologies.

Carter, et al., "Platelet-Rich Plasma Gel Promotes Differentiation and Regeneration During Equiine Wound Healing," Experimental and Molecular Pathology 74 (2003) 244-255; www.sciencedirect.com.

V. Vila, et al., "Assessment of The Thrombin Generation Assay in Haemophilia: Comparative Study Between Fresh and Frozen Platelet-Rich Plasma," Haemophilia, Mar. 2013; 19(2):318-21. DOI: 10.111/hae.12044. Epub Nov. 23, 2012; http://www.ncbi.nlm.nih.gov/pubmed/23174035.

Alice Roffi, et al., Research Article, "Does Platelet-Rich Plasma Freeze-Thawing Influence Growth Factor Release and Their Effects on Chondrocytes and Synoviocytes?," Hindawi Publishing Company, BioMed Research International, vol. 2014, Article ID 692913, 10 pages, http://dx.doi.org/10.1155/2014/692913.

Yu Nakajima, et al., "Bioactivity of Freeze-Dried Platelet-Rich Plasma in an Absorbed Form of a Biodegradable Polymer Material," Platelets, vol. 23, Issue 8, 2012; http://www.tandfonline.com/doi/abs/10.3109/09537104.2011.645923.

Giuseppe Lippi, et al., "Reliability of The Trombin-Generation Assay in Frozen-Thawed Platelet-Rich Plasma," Clinical Chemistry 52, No. 9, 2006, p. 1827-1828.

Jain, N.C. and Kono, C.S.(1980), "The Platelet Factor-3 Test for Detection of Canine Antiplatelet Antibody," Veterinary Clinical Pathology, 9: 10-14 doi: 10.1111/j.1939-165X.1980.tb00886.x.

Shuan Shian Huang, et al., "Proteoglycan Carrier of Human Platelet Factor 4, Isolation and Characterization," The Journal of Biological Chemistry, vol. 257, No. 19, Issue of Oct. 10, pp. 11546-11550, 1982.

Makoto Horimizu, et al., "An Improved Freeze-Dried PRP-Coated Biodegradable Material Suitable for Connective Tissue Regenerative Therapy," Cryobiology, vol. 66, Issue 3, Jun. 2013, pp. 223-232; http://www.sciencedirect.com/science/article/pii/50011224013000278.

Nathalie Hezard, et al., "Utility of Thrombin-Generation Assay in the Screening of Factor V G1691A (Leiden) and Prothrombin G20210A Mutations and Protein S Deficiency," Hemostasis and Thrombosis, Clinical Chemistry 52:4, 665-670 (2006).

Pietramaggiori, G., et al., "Freeze-Dried Platelet-Rich Plasma Shows Beneficial Healing Properties in Chronic Wounds," Wound Repair Regen, Sep.-Oct. 2006; 14(5):573-80.

Ismail Elalami and Meyer M. Samama, Original basic research, "Towards a Standarization of Thrombin Generation Assessment; The Influence of Tissue Factor, Platelets and Phospholipids Concentration on The Normal Values of Thrombogram-Thrombinoscope Assay," Thrombosis Journal 2005, 3:16 doi:10.1186/1477-9560-3-16. Published Oct. 26, 2005.

Zoku, et al., "ZOKU MiniPops Instruction Manual," Dec. 31, 2013, XP055451993, retrieved from the internet: URL:https://cdn.shopify.com/s/files/1/0038/1592/files/Mini-Pops.pdf?1442 [retrieved on Feb. 16, 2018].

* cited by examiner

COMBINED AUTOLOGOUS BIOLOGIC AND COLD THERAPY TREATMENT OF SKIN INJURIES

BACKGROUND

This disclosure relates to a method and apparatus for treating skin injuries or other superficial wounds. Autologous blood components may be frozen in a plurality of individual doses. Each dose can subsequently be applied in frozen form to treat skin injuries.

Healing injuries involves a complex series of events where proteins in the blood called growth factors are released to signal for the healing process to begin. Many growth factors are derived from small blood cells called platelets. Increased growth factor levels improve the recruitment of cells to an injury site and optimize the environment for healing. Accordingly, autologous blood components that are derived from the patient, such as platelet rich plasma, have been used in various surgical procedures to provide a concentrated level of beneficial growth factors at the point of care.

SUMMARY

This disclosure describes a combined autologous biologic and cold therapy treatment for treating various skin injuries. The treatment may include applying autologous blood components, including but not limited to platelet rich plasma, to a skin injury in a manner that influences the healing process.

A tray assembly for freezing autologous blood components according to an exemplary aspect of the present disclosure includes, among other things, a tray body and a plurality of compartments formed in the tray body, each of the plurality of compartments configured to receive an individual dose of an autologous blood component.

In a further non-limiting embodiment of the foregoing tray assembly, the autologous blood component includes platelet rich plasma.

In a further non-limiting embodiment of either of the foregoing tray assemblies, a rack is received over the tray body to at least partially cover each of the plurality of compartments.

In a further non-limiting embodiment of any of the foregoing tray assemblies, at least one handle is removably connected to the rack.

In a further non-limiting embodiment of any of the foregoing tray assemblies, a handle extends into each of the plurality of compartments.

In a further non-limiting embodiment of any of the foregoing tray assemblies, a first portion of the handle extends into each of the plurality of compartments and a second portion of the handle protrudes outwardly from each of the plurality of compartments.

In a further non-limiting embodiment of any of the foregoing tray assemblies, the tray body is made from a flexible material.

In a further non-limiting embodiment of any of the foregoing tray assemblies, the flexible material includes silicone.

In a further non-limiting embodiment of any of the foregoing tray assemblies, a label is affixed to the tray body and configured to inscribe patient information.

In a further non-limiting embodiment of any of the foregoing tray assemblies, a handle extends from the tray body.

In a further non-limiting embodiment of any of the foregoing tray assemblies, a handle extends into each of the plurality of compartments, and each handle includes a label for inscribing patient information.

In a further non-limiting embodiment of any of the foregoing tray assemblies, a surface of the tray body circumscribes each of the plurality of compartments.

A surgical method according to another exemplary aspect of the present disclosure incomes, among other things, freezing an autologous blood component in a plurality of individual doses using a tray assembly that includes a plurality of compartments each configured to receive one of the plurality of individual doses.

In a further non-limiting embodiment of the foregoing method, the method includes harvesting a blood sample from a patient prior to the step of freezing the autologous blood component.

In a further non-limiting embodiment of either of the foregoing methods, the method includes separating the autologous blood component from the blood sample prior to the step of freezing the autologous blood component.

In a further non-limiting embodiment of any of the foregoing methods, the method includes applying a first dose of the plurality of individual doses to a skin injury while the first dose in still frozen.

In a further non-limiting embodiment of any of the foregoing methods, the method includes removing the first dose from the tray assembly using a handle at least partially imbedded inside the first dose.

The embodiments, examples and alternatives of the preceding paragraphs, the claims, or the following description and drawings, including any of their various aspects or respective individual features, may be practiced independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes a surgical technique for treating skin injuries. The surgical technique includes applying autologous blood components, such as platelet rich plasma, to a skin injury to influence the healing process.

In some embodiments, the surgical technique includes freezing an autologous blood component in a plurality of individual doses and later applying a dose of the plurality of individual doses to a skin injury while the dose is still frozen. Various tray assembly designs may be utilized to separate and freeze the autologous blood components in the plurality of individual doses. These and other features are described in greater detail in the following paragraphs of this detailed description.

Figure 1A:
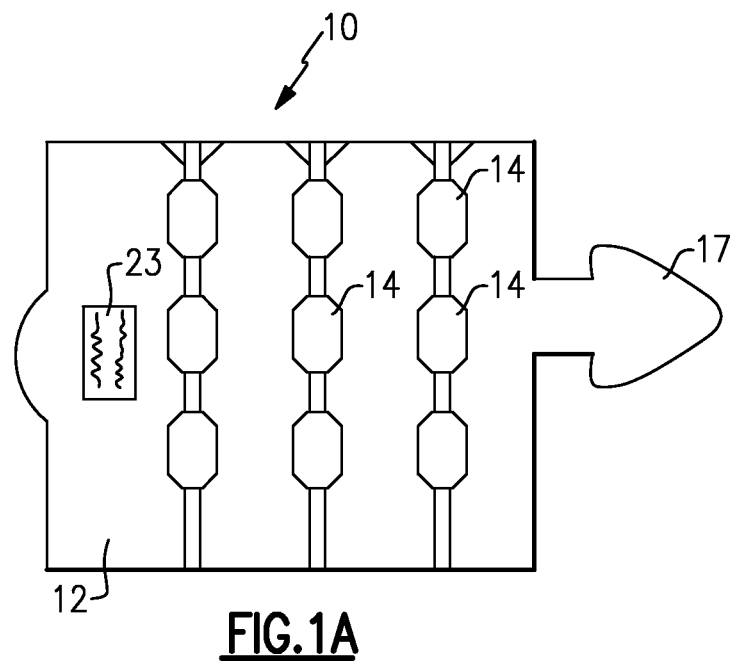
FIGS. 1A and 1B illustrate a tray assembly for freezing an autologous blood component according to a first embodiment of this disclosure.
Figure 1B:
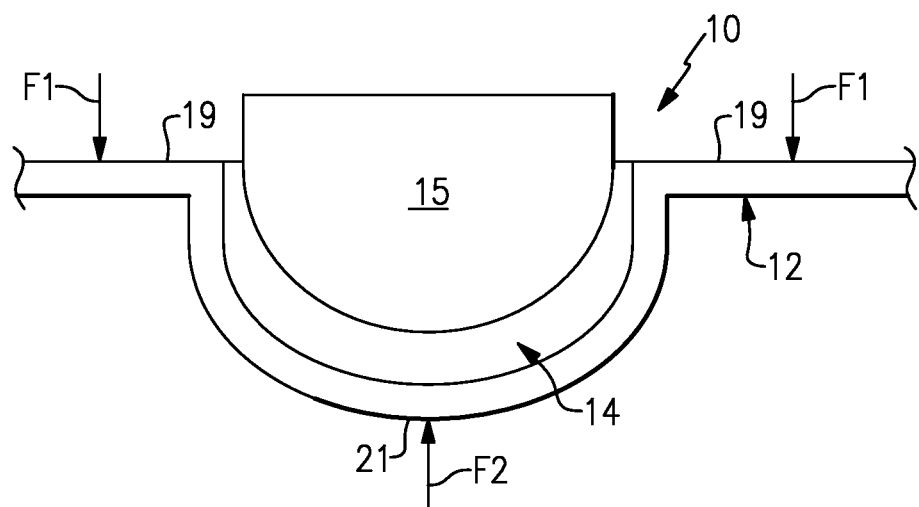

FIGS. 1A and 1B illustrate a tray assembly 10 configured for freezing autologous blood components. The autologous blood components described in this disclosure may be a fluid or composition that includes platelet rich plasma, platelet-poor plasma, bone marrow aspirate, bone marrow concentrate and stem cells, or any other platelet enriched blood components or combinations of blood components. The autologous blood components may have a platelet concentration that is greater than that found in a patient's whole blood. The autologous blood components may also include certain growth factors. Non-limiting examples of growth factors include platelet derived growth factor, fibroblast growth factor, transforming growth factor β, transforming growth factor α, and epithelial growth factor.

The exemplary tray assembly 10 may include a tray body 12 having a plurality of compartments 14. Each compartment 14 is sized and shaped to receive a single, individual dose 15 (see FIG. 1B) of an autologous blood component. In the illustrated non-limiting embodiment, the tray body 12 includes nine compartments 14 that act as individual receptacles for receiving a single dose of an autologous blood component. However, a greater or fewer number of compartments may be employed by the tray assembly 10 within the scope of this disclosure.

In another non-limiting embodiment, the tray body 12 may additionally include a handle 17 for handling and/or transporting the tray assembly 10. In yet another non-limiting embodiment, one or more labels 23 are provided on the tray body 12. The labels 23 may be used for inscribing patient information, such as to identify the patient, for example.

The tray body 12 may be made of a non-rigid or flexible material. Silicone is one suitable flexible material that could be employed to construct the tray body 12. However, other materials could alternatively be utilized within the scope of this disclosure.

Referring now primarily to FIG. 1B, the tray body 12, including each compartment 14, may be bent, flexed, or otherwise manipulated in order to remove a dose 15, which may be in frozen form, of the autologous blood component from the compartment 14. For example, in one non-limiting embodiment, a force F1 may be applied to surfaces 19 of the tray body 12 that surround or circumscribe the compartment 14. At the same time the forces F1 are applied, a force F2 may be applied to a bottom surface 21 of the compartment 14 to remove the dose 15 from the compartment 14. The dose 15 can subsequently be used to treat a skin injury, as further discussed below.

Figure 2:
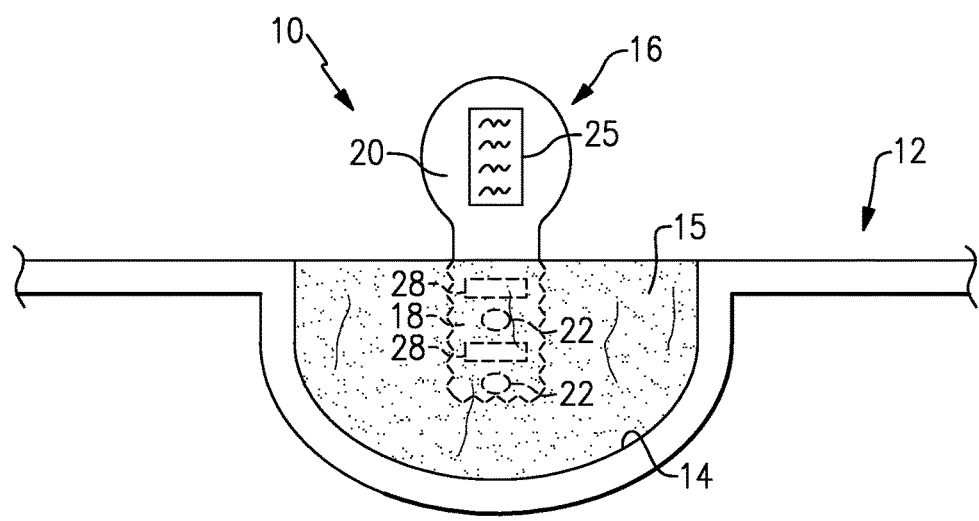
FIG. 2 illustrates a tray assembly according to a second embodiment of this disclosure.

In another non-limiting embodiment, shown in FIG. 2, a handle 16 may extend into each compartment 14 to aid in removal of the dose 15 of the frozen autologous blood component from the tray assembly 10. In other words, a single handle 16 may extend into each compartment 14 of the tray assembly 10 to aid in removing each dose 15. In one non-limiting embodiment, each handle 16 includes a first portion 18 that extends inside the compartments 14 (i.e., inside the dose 15) and a second portion 20 that protrudes outwardly of each compartment 14. The first portions 18 of each handle 16 may include one or more openings 22 and one or more ribs 28 that are configured to improve the bond between the dose 15 and the handle 16 as the dose 15 freezes around the handle 16. In another non-limiting embodiment, a label 25 may be affixed to the handle 16 for inscribing various patient information.

Figure 3A:
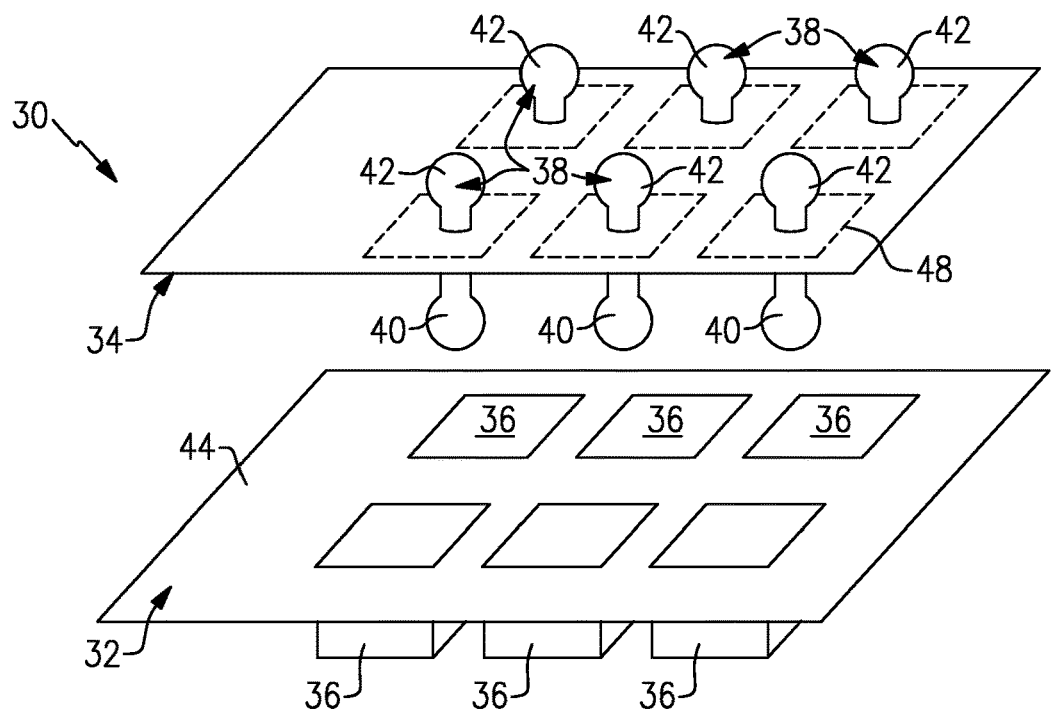
FIGS. 3A and 3B illustrate a tray assembly according to yet another embodiment of this disclosure.
Figure 3B:
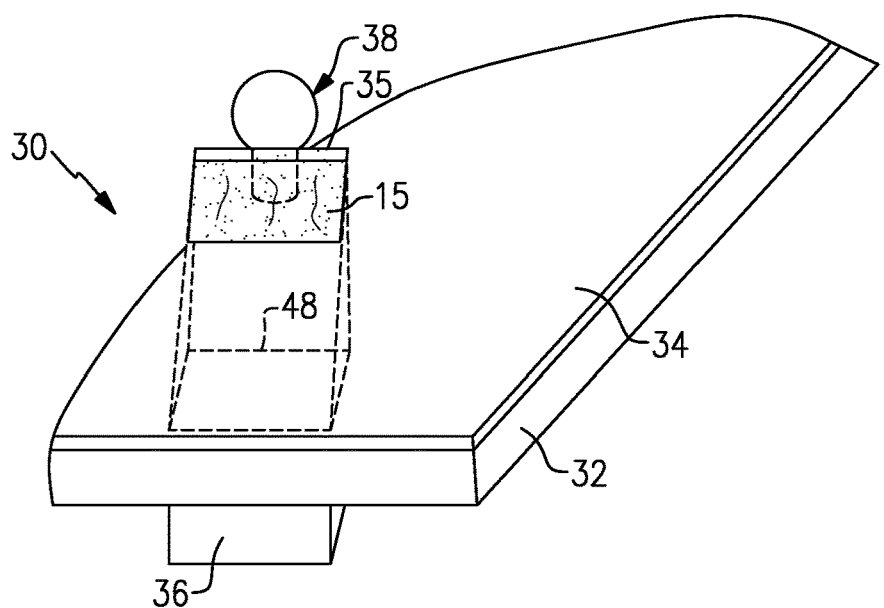

FIGS. 3A and 3B illustrate another exemplary tray assembly 30 for receiving and freezing individual doses of autologous blood components. The tray assembly 30 includes a tray body 32 and a rack 34 that can be placed over the tray body 32. The tray body 32 includes a plurality of compartments 36 for receiving individual doses of an autologous blood component for subsequent freezing of the individual doses. In one non-limiting embodiment, each compartment 36 is thimble shaped and is sized to be approximately one centimeter in length by one centimeter in width by one centimeter in depth (i.e., one centimeter cubed). However, other shapes and sizes are also contemplated.

In another non-limiting embodiment, the rack 34 is positioned over top of the tray body 32 to at least partially cover the compartments 36. The rack 34 may simply rest on a top surface 44 of the tray body 32 or could be removably secured to the tray body 32 in any known manner.

The rack 34 may additionally include a plurality of handles 38 that extend into the compartments 36 once the rack 34 is positioned over the tray body 32. The rack 34 centers each handle 38 within its respective compartment 36 and maintains a positioning of each handle 38 prior to freezing the autologous blood components. In one non-limiting embodiment, each handle 38 includes a first portion 40 that extends from a first side of the rack 34 and into the one of the compartments 36 and a second portion 42 that extends from an opposite side of the rack 34 in a direction away from the compartments 36.

Referring now primarily to FIG. 3B, each handle 38 may be removed from the rack 34 to remove a dose 15 of a frozen autologous blood component from the tray body 32. For example, each handle 38 could be removed about a perforation 48 formed in the rack 34. Removal of a portion of the rack 34 that is circumscribed by the perforation 48 forms a collar 35 of each handle 38. In one non-limiting embodiment, the collars 35 of each handle 38 snap into the rack 34 about the perimeter of the perforations 48 such that the collars 35 are disposed directly above the compartments 36.

Figure 4:
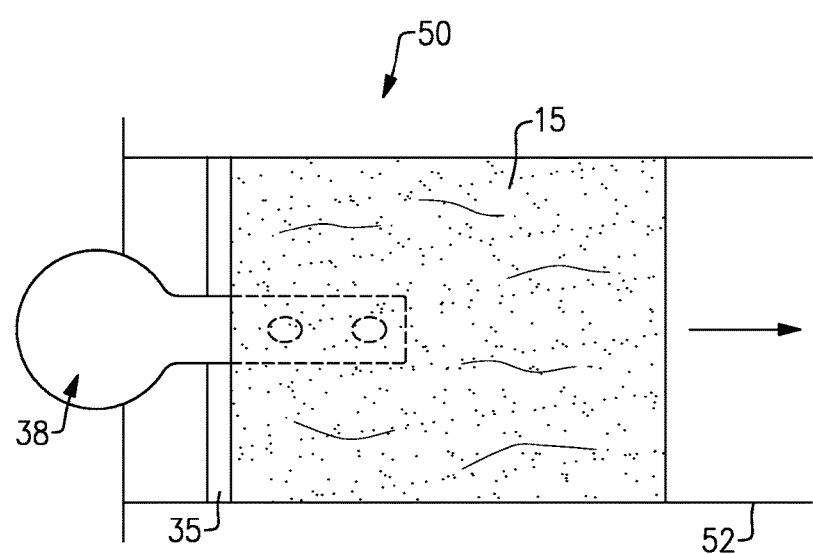
FIG. 4 illustrates an applicator device for applying a frozen dose of an autologous blood component to a skin injury.

FIG. 4 illustrates an exemplary applicator device 50 for applying a frozen autologous blood component to a skin injury. The applicator device 50 may include a tube 52 configured to receive an autologous blood component. For example, in one non-limiting embodiment, the tube 52 may receive a frozen dose 15 of an autologous blood component. A handle 38 may be attached to the frozen dose 15, and the frozen dose 15 may be pushed through the tube 52 using the handle 38 to apply the frozen dose 15 to a skin injury. In one non-limiting embodiment, the collar 35 of the handle 38 applies a force against frozen dose 15 to move it within the tube 52. The frozen dose 15 of the autologous blood component provides pain and inflammation cold therapy, and as the frozen dose 15 slowly melts, the appliation device 50 applies the autologous blood component to the treatment site with ideal distribution over a relatively broad area similar to a popsicle-like applicator.

FIGS. 5-9, with continued reference to FIGS. 1-4, schematically illustrate an exemplary surgical technique for treating a skin injury using frozen autologous blood components. In this disclosure, the term "skin injury" is intended to denote any type of skin injury or wound resulting from tearing, cutting and/or puncturing the skin. In one non-limiting embodiment, the skin injury is a superficial skin injury that is generally limited to the outer layers of the skin. FIGS. 5 through 9 illustrate, in sequential order, one non-limiting embodiment for performing a surgical technique to treat a skin injury. It should be understood; however, that fewer or additional steps than are recited below could be performed and that the recited order of steps is not intended to limit this disclosure.

Figure 5:
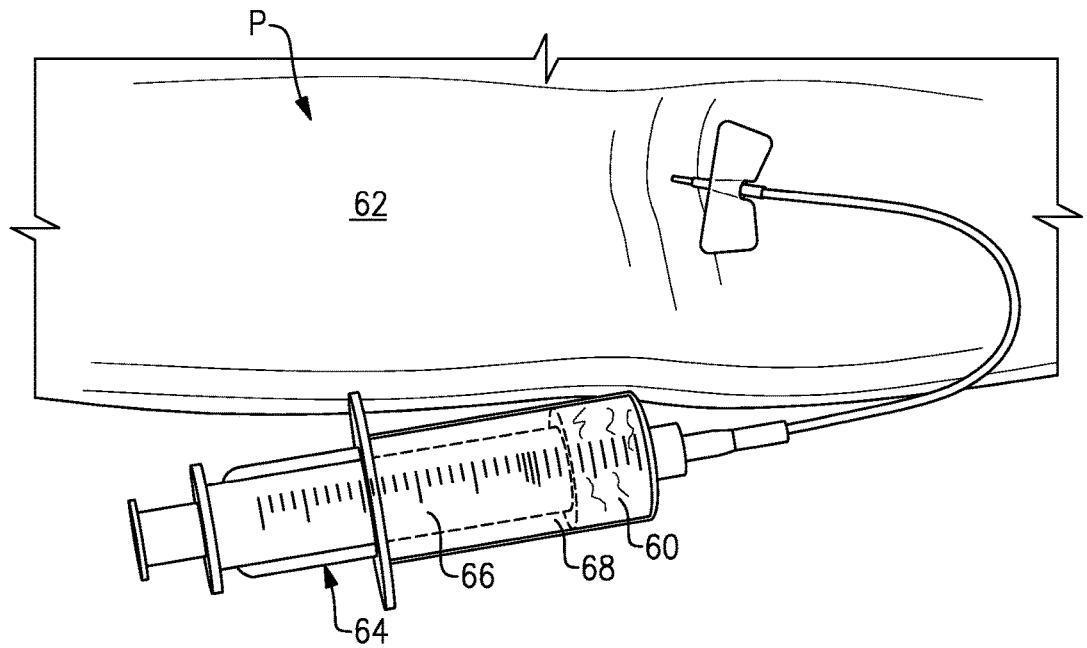
FIG. 5 schematically illustrates harvesting a blood sample from a patient.

Referring first to FIG. 5, a blood sample 60 may be harvested from a body 62 of a Patient P. The blood sample 60 may be harvested from venous whole blood of the Patient P. In one non-limiting embodiment, the blood sample 60 is a sample of approximately 10 ml of blood and is harvested using a double chamber syringe 64 that includes an inner chamber 66 and an outer chamber 68. An anticoagulant, such as ACD-A anticoagulant citrate dextrose solution, may optionally be added to the double chamber syringe 64 prior to obtaining the blood sample 60. The blood sample 60 is initially collected within the outer chamber 68 of the double chamber syringe 64.

Figure 6:
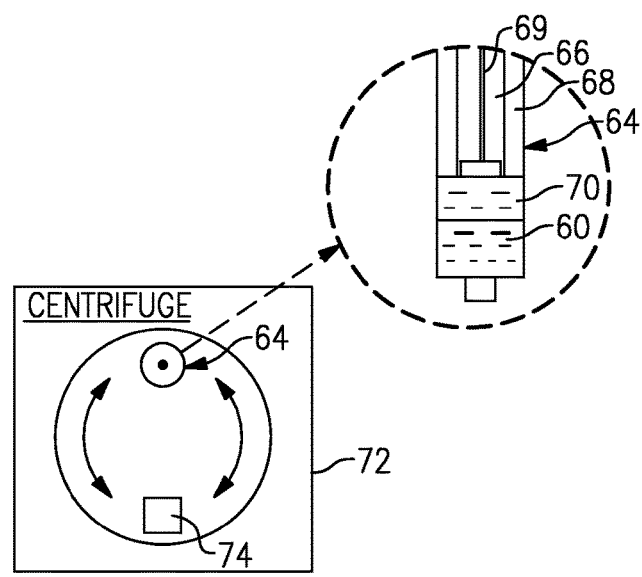
FIG. 6 schematically illustrates separation of an autologous blood component from the blood sample.

Next, as shown in FIG. 6, an autologous blood component 70 may be separated from the blood sample 60. This separation can be achieved using a centrifuge 72 (shown schematically) or by using other known separating techniques. In one non-limiting embodiment, the double chamber syringe 64 and an appropriate counterbalance 74 are inserted into the centrifuge 72 and then spun at approximately 1500 RPM for around five minutes to separate the autologous blood component 70 from the blood sample 60. Once separated, the autologous blood component 70 can be extracted from the outer chamber 68 into the inner chamber 66 of the double chamber syringe 64 via a plunger 69. The inner chamber 66 can then be removed from the outer chamber 68 of the double chamber syringe 64.

Figure 7:
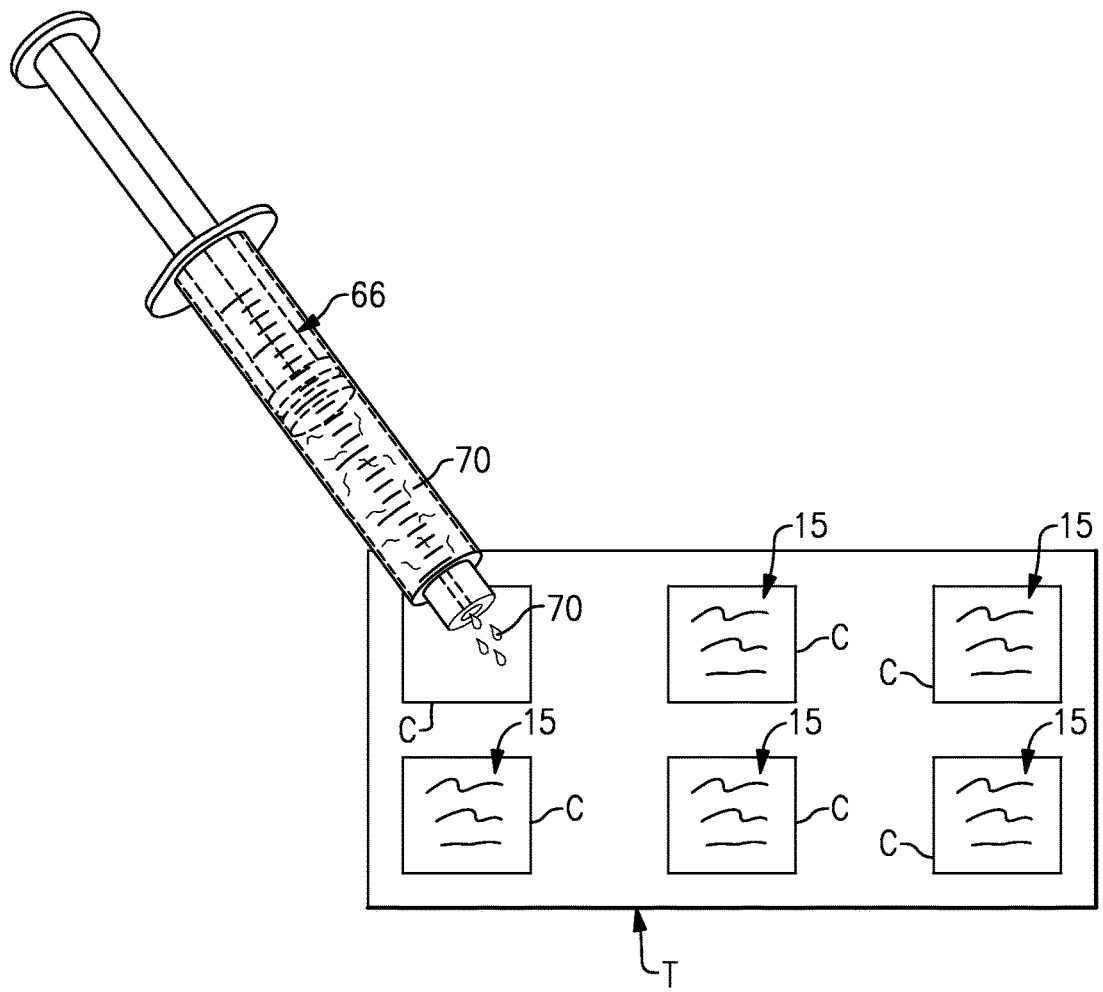
FIG. 7 schematically illustrates injection of the autologous blood component into a plurality of individual compartments of a tray assembly.
Figure 8:
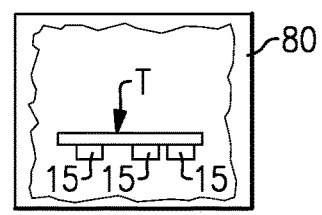
FIG. 8 schematically illustrates freezing the autologous blood components in a tray assembly.

Referring to FIG. 7, the autologous blood component 70 may next be divided into a plurality of individual doses 15 by injecting a portion of the autologous blood component 70 into each compartment C of a sterile tray assembly T. The inner chamber 66, which is removable from the double chamber syringe 64, may be used to inject the autologous blood components 70 into each compartment C. The tray assembly T may be configured like any of the tray assemblies described above to store multiple doses of the autologous blood component 70.

The individual doses 15 may then be frozen in the tray assembly T for later use. This is shown schematically in FIG. 8. In one non-limiting embodiment, the tray assembly T may be positioned within a freezer 80 to freeze the individual doses 15 of the autologous blood component 70. In another embodiment, the individual doses 15 may be rapidly frozen within the tray assembly T using liquid nitrogen or dry ice. Other freezing methodologies could also be used to freeze the individual doses 15 of the autologous blood component 70.

Figure 9:
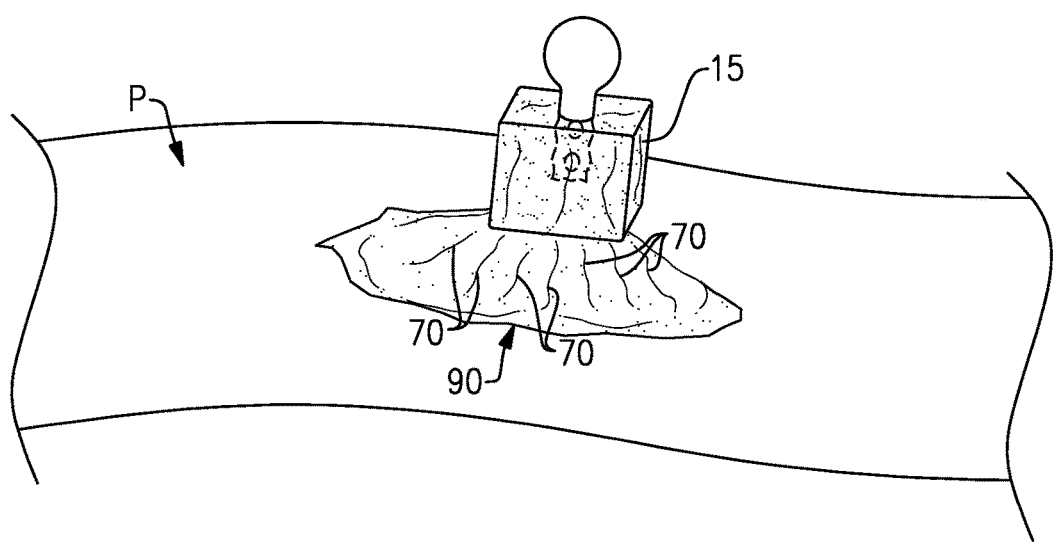
FIG. 9 schematically illustrates the use of a frozen dose of an autologous blood component for treating a skin injury of the patient.

Referring now primarily to FIG. 9, one of the individual doses 15 of the frozen autologous blood component 70 may be removed from the tray assembly T when subsequently needed for treating a skin injury 90 of the Patient P. The skin injury 90 may be located anywhere on the Patient P. In one non-limiting embodiment, the Patient P is the same patient from which the autologous blood component 70 was originally harvested.

The individual dose 15 may be applied to the skin injury 90 in frozen form to provide a combined autologous biological and cold therapy treatment for treating the skin injury 90. For example, the individual dose 15 of the frozen autologous blood component 70 initially provides pain and inflammation cold therapy to the skin injury 90, and as the individual dose 15 slowly melts, the autologous blood component 70 is distributed over the skin injury 90. The high level of platelets and associated growth factors of the autologous blood component 70 triggers initiation of the healing process and may enhance healing of the skin injury 90 as well as promote tissue growth. The remaining individual doses 15 of the autologous blood component 70 may be kept frozen for later use to treat the same skin injury or other superficial skin injuries or wounds.

A 4 to 5 cc harvest of autologus blood components can create up to six or more frozen dosage treatments that lower treatment costs, reduce the necessity to withdraw blood during subsequent doctor office visits, and speed up treatment since the patient can apply the frozen doses themselves either alone in an exam room, locker room or even at home. Finally, although described individually above, the various tray assemblies, handles, applicators, syringes, etc. described herein may be part of a surgical instrumentation set or kit for treating skin injuries.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method, comprising:
   harvesting a blood sample from a patient;
   separating an autologous blood component from the blood sample;
   injecting an individual dose of the autologous blood component into each of a plurality of compartments of a tray assembly, wherein the tray assembly includes a tray body that establishes the plurality of compartments, a rack removably connected to the tray body, and a plurality of handles removably connected to the rack, wherein one handle of the plurality of handles extends into each of the plurality of compartments;
   positioning the tray assembly within a freezer to freeze the individual doses of the autologous blood component;
   removing a first dose of the individual doses from the tray assembly, wherein removing the first dose of the individual doses includes removing a first handle of the plurality of handles from the rack; and applying the first dose to a skin injury in frozen form, wherein applying the first dose to the skin injury initially provides cold therapy to the skin injury, and as the first dose melts, the autologous blood component is distributed over the skin injury to promote healing.

2. The method as recited in claim 1, wherein the one handle of the plurality of handles includes a collar that completely covers each of the plurality of compartments that contains the first dose when the one handle is connected to the tray assembly.

* * * * *